United States Patent
Strong et al.

(10) Patent No.: US 9,326,961 B2
(45) Date of Patent: May 3, 2016

(54) DIET AND METHODS FOR IMPROVING LEARNING CAPACITY, MOOD AND BEHAVIOR IN MAMMALS

(75) Inventors: Valerie Strong, Sheffield (GB); Peter Neville, Salisbury (GB)

(73) Assignee: COAPE, LTD, Salisbury, Wiltshire (GB)

( * ) Notice: Subject to any disclaimer, the term of this patent is extended or adjusted under 35 U.S.C. 154(b) by 335 days.

(21) Appl. No.: 12/931,888

(22) Filed: Feb. 14, 2011

(65) Prior Publication Data

US 2011/0212888 A1 Sep. 1, 2011

Related U.S. Application Data

(60) Provisional application No. 61/339,067, filed on Feb. 26, 2010.

(51) Int. Cl.

| | |
|---|---|
| *A23L 1/29* | (2006.01) |
| *A23L 1/305* | (2006.01) |
| *A61K 31/4415* | (2006.01) |
| *A61K 31/198* | (2006.01) |
| *A23K 1/16* | (2006.01) |
| *A23K 1/18* | (2006.01) |
| *A61K 45/06* | (2006.01) |

(52) U.S. Cl.
CPC .............. *A61K 31/198* (2013.01); *A23K 1/1634* (2013.01); *A23K 1/1643* (2013.01); *A23K 1/1806* (2013.01); *A23K 1/1846* (2013.01); *A23L 1/296* (2013.01); *A23L 1/305* (2013.01); *A23L 1/3051* (2013.01); *A61K 31/4415* (2013.01); *A61K 45/06* (2013.01)

(58) Field of Classification Search
CPC ... A23K 1/1631; A23K 1/1643; A23K 1/143; A23K 1/1846; A23K 1/1806; A61K 2300/00; A61K 38/02; A61K 38/16
See application file for complete search history.

(56) References Cited

U.S. PATENT DOCUMENTS

| | | |
|---|---|---|
| 4,753,804 A | 6/1988 | Iaccheri et al. |
| 4,897,380 A | 1/1990 | Pollack et al. |
| 5,360,614 A | 11/1994 | Fox et al. |
| 5,760,014 A | 6/1998 | Wurtman |
| 5,762,960 A | 6/1998 | Dodman |
| 6,218,420 B1 | 4/2001 | Dioguardia |
| 6,410,522 B1 | 6/2002 | Ruenberg |
| 6,440,485 B1 | 8/2002 | Cheuk et al. |
| 6,783,792 B2 | 8/2004 | McDaniel, III et al. |
| 6,866,874 B2 | 3/2005 | Hudson et al. |

FOREIGN PATENT DOCUMENTS

WO WO 2006130567 A2 * 12/2006

OTHER PUBLICATIONS

Benders et al., "High Doses of Vitamin B6 in the Rat are Associated with Inhibition of Hepatic Tryptophan Metabolism and Increased Uptake of Tryptophan in the Brain", Journal of Neurochemistry, 1984, pp. 733-736.*
Fernstrom et al., "Brain tryptophan concentrations and serotonin synthesis remain responsive to food consumption after the ingestion of sequential meal", The American Journal of Clinical Nutrition, 1995; pp. 312-319.*
Muthayya et al., "Consumption of a mid-morning snack improves memory but not attention in school children", Physiology and Behavior, 2007, pp. 142-150.*
Yokogoshi, "Acute effects of various carbohydrates on brain serotonin metabolism and catecholamines of rats", Nutrition reports international, 1998; abstract obtained from AGRICOLA on Nov. 13, 2013; p. 1.*
USDA National Nutrient Database for Standard ReferenceRelease 27; Basic Report 20093, Pasta, fresh-refrigerated, plain, as purchased; Report Date:Sep. 30, 2014 20:31 EDT; pp. 1-2.*
USDA National Nutrient Database for Standard ReferenceRelease 27; Basic Report 11362, Potatoes, raw, skin; Report Date:Sep. 30, 2014 20:30 EDT; pp. 1-2.*
U.S. Appl. No. 10/218,500, filed Aug. 14, 2002, Cheuk, W.E., et al.
U.S. Appl. No. 11/813,119, filed Dec. 29, 2005, Wedeking, K. J.
U.S. Appl. No. 12/734,014, filed Oct. 2, 2008, Pan, Y. et al.
Davis "Carbohydrates, branched-chain amino acid . . . : the central fatigue hypothesis," Internat. of Sport Nutrition, Human Kinetics Pub, Champaign, IL 1995 vol. 5:S29-38.
Dodman et al. "Effect of Dietary Protein,,, on Behavior in Dogs." J. AVMA, 1996, vol. 208, 376-379.
Deanopoli et al.: "Effect of Dietary Protein . . . and tryptophan . . . in dogs." 2000. J. AVMA, vol. 217,:504, tables 1,2, pp. 504-508.
Fretwall, et al.: "Effect of . . . branched-chain amino acids . . . cognitive function in active dogs." J. Nutrition. 2006. vol. 136:2069s-2071S.
Bosch et al.: "Impact of nutriton on canine behaviour." Research Reviews, 2007. vol. 20:180-194.
Wikipedia, "Labrador Retriever" First page only, Mar. 16, 2014.

* cited by examiner

*Primary Examiner* — Lianko Garyu
(74) *Attorney, Agent, or Firm* — Kathleen R. Terry

(57) ABSTRACT

This invention provides a method of improving mood and learning capacity in a mammal by giving the mammal a meal of low protein food, followed by a second meal of high glycemic index carbohydrate. A composition to be given to a mammal to improve mood and learning capacity and to reduce aggressive behavior contains at least one tyrosine uptake competitive amino acid in a ratio of 0.5% to 2% to protein. The tyrosine competitive amino acid preferred is leucine, isoleucine or valine.

8 Claims, No Drawings

DIET AND METHODS FOR IMPROVING LEARNING CAPACITY, MOOD AND BEHAVIOR IN MAMMALS

CROSS REFERENCE TO RELATED APPLICATIONS

This application is related to and takes priority from U.S. Provisional Patent Application Ser. No. 61/339,067, filed Feb. 26, 2010.

BACKGROUND OF THE INVENTION

Appropriate nutrition requires that all nutrients, carbohydrates, lipids, proteins, minerals, vitamins and water are ingested in adequate amounts and in the correct proportions. This is essential for normal organ development and function, reproduction, repair of body tissues and combating stress and disease. The nutrient intake must also be adjusted for varied levels of activity and physical work. Beyond those basic elements, however, it has been found that diet, particularly protein intake, has a profound effect on learning, behavior and mood.

It has been shown in humans and other species that certain amino acids directly influence brain activity and behavior by enhancing or reducing the rate of synthesis of various neurotransmitters. Noradrenaline induces high states of arousal and has been implicated in the generation of aggressive behavior. Dopamine is involved in motor coordination, attention, reinforcement and reaction time. Serotonin plays a role in the regulation of mood, the control of sleep and arousal, the regulation of pain and in the control of eating. Low serotonin levels have been demonstrated in individuals showing impulsivity, aggressive behavior, anti-social behavior, attention deficit/hyperactivity disorder, agitation, anxiety and learning problems. A lack of serotonin may cause a reduction in the ability to learn new or alternative behaviors.

Ingested protein is broken down into its component amino acids. It is well known that the amino acids tryptophan and tyrosine are converted to neurotransmitters in the mammalian brain. Tyrosine is converted to the catecholamine stimulants adrenaline, dopamine and noradrenaline, while tryptophan is converted to serotonin. The balance between the two families of neurotransmitters defines the mood of the mammal. A tip in the balance toward catecholamine is manifested in certain forms of aggression and hyperactivity, while high serotonin levels tend to induce calmness.

Most of the studies have been done in humans, although corollaries can be noted to other species. The canine corollaries to human findings may exhibit as aggression, anxiety, over activity/excitability, the inability to learn new behaviors and general touch sensitivity. In other words, the balance has been tipped to the catecholamines.

Humans and dogs experiencing emotional disorders have been treated to raise serotonin levels by tryptophan supplementation or by administration of serotonin reuptake inhibitors, which increase the dwell time on neural synapses, thus increasing the serotonin effect. U.S. Pat. No. 5,762,960, issued Jun. 9, 1998, discloses the use of several known serotonin reuptake inhibitors to reduce aggression in dogs. Conversely, Wurtman in U.S. Pat. No. 4,435,424, issued May 6, 1984, suggests the benefits of adding tyrosine to the diet of humans in order to raise catecholamines in low-energy subjects. This use of administered drugs to change the balance of catecholamines to serotonin is well known in both medical and veterinary practice.

Whatever the treatment, the patient must ingest a good balanced diet, a diet that provides sufficient energy as well as sources of monoamines for brain function. It is well known that the brain is very sensitive to any change in the level of sugar in the blood, and therefore this is usually under very careful control. However, if there is a fault in the mechanism controlling the levels of blood sugar, which then fall to a hypoglycemic state, the function of the brain becomes impaired and certain physical and behavioral changes take place. Following a meal, the level of sugar in the blood rises, in response to which, insulin is secreted and glucose diverted to the liver where it is stored as glycogen. The process is reversed when blood sugar levels are low. The liver continually secretes glucose back into the blood to convert to energy which is vital to life functions. The amount of glycogen stored in the liver is insufficient to maintain normal blood sugar levels for more than a short time. During periods of deprivation of blood glucose, the tissues gain their energy from various non-carbohydrate source but this deprives the brain of amino acids to be converted to neurotransmitters.

Dogs can thrive on a large number of very different food materials. Although classed in the order Carnivora, dogs are not strict carnivores, but like humans, are omnivorous and able to utilize nutrients from plant sources as well as animal sources. Carnivores are generally considered to be once-a-day, or less often feeders, gorging when food is available and fasting in between feasts. This is suitable for life in the wild. Many domestic pets are fed once a day, mimicking the case of the wild carnivore. The large daily meal is followed by a period of torpor and then by a period of increased activity. These mood swings are not compatible with indoor life as a pet and are considered to result in behavior problems.

Some dogs may not be able to tolerate periods of fasting, due to impaired liver function or inadequate diet to provide energy requirements. Each dog's dietary and exercise requirements are different and their ability to utilize constituents of their diet will vary. These factors have a direct influence on behavior. For example, low blood sugar can result in a reduced level of response, shallow breathing, muscle tremors and a change from normal behavior to confusion, agitation and aggression.

In assessing behavior problems, low blood sugar levels could give an indication of the underlying cause when no other has been identified. Low blood sugar levels may be partly responsible for the frequently observed aggressive state in dogs awakening abruptly from deep sleep, a time at which the brain has insufficient energy to make rational decisions, which the primitive basic survival instincts of fight/flight are active.

Dog owners need a simple dietary regimen to stabilize and improve the learning capability, mood and behavior of their dogs without reliance on pharmacological intervention. Similarly, felines, horses and humans can benefit from such simple regimens, which can easily be integrated into daily care. It is desirable to find a way to mimic a dietary regimen by supplementation of the diet.

SUMMARY OF THE INVENTION

The methods and compositions of this invention were designed to assist mammals which, when domesticated, are forced to alter their natural behavioral repertoires, in order to resolve the resulting conflicts between normal behavior and that which is expected of a domestic animal. For purposes of illustration, the dog has been selected as the test animal for the teachings of this application, but it is understood that the principles of this invention may also be applied to other mammals, including domestic felines, horses and humans.

A simple regimen has been developed to stabilize and improve the learning capacity, mood and behavior of canines by regulating the level of glucose in the brain and ensuring optimum levels of monoamine neurotransmitters, particularly serotonin. In the morning, the dog is fed a first meal having a low protein content. By low protein, it is intended to mean a diet with 16% to 26% protein, most preferably 22%. The protein is selected from high quality protein such as lamb, poultry and chicken meats and is adequate to support growth and maintenance in the dog. The diet is supplemented with from 0.05 to 10 mg/kg body weight of vitamin B6, most preferably 0.08 to 1.5 mg/kg body weight.

For best stabilization of mood, approximately three hours after ingestion of the first meal, the dog is fed a second meal, consisting of approximately one-half to four ounces dry weight of carbohydrate, depending on the size of the dog. By way of example, the second meal for a Labrador is about two ounces. The preferred carbohydrate is one that is palatable to the dog, easily provided, and rapidly converted to sugars and taken up into the blood stream that is, has a high glycemic index. A preferred carbohydrate is pasta or potatoes.

The first meal and second meal are repeated about 8 to 12 hours later. It is recommended that a dog should remain on this regimen for up to three months, during which time other behavioral and training exercises should be undertaken, to allow sufficient time for new responses to be fully learned.

A complete diet is provided for those dog owners who are unable or unwilling to follow a regimen. The diet will preferably contain a low protein content, with between 16 and 26% w/w content, preferably between 20% and 24% dry weight protein content and most preferably 22%. The protein is selected from high quality protein such as lamb, poultry and chicken meats and is adequate to support growth and maintenance in the dog. The diet is supplemented with sufficient vitamin B6 to supply from 0.05 to 10 mg/kg body weight of vitamin B6, most preferably 0.08 to 1.5 mg/kg body weight. A time release carbohydrate at a concentration of about one % to four % of total dry weight of the diet may be incorporated into the diet to mimic the second meal. This time release carbohydrate is selected to be released approximately three hours after ingestion and to have a high glycemic index. It is well known in the art to select appropriate methods and materials to prepare such a time release carbohydrate.

The regimen may be mimicked by feeding a diet further supplemented with from 0.5 to 2% neutral branched-chain amino acids selecting from the group consisting of leucine, isoleucine and valine. These amino acids compete with the transport of tyrosine across the blood-brain barrier, thus effectively tipping the catecholamine/serotonin balance toward serotonin.

A representative diet having an energy density of 378 kcal/100 gram wet weight consists of:

| LOW PROTEIN DIET | |
|---|---|
| crude protein | 20% (16.5%-26%) |
| crude oil | 18% (16%-20%) |
| carbohydrate | 43% (20%-60%) |
| moisture | 8% (2%-10%) |
| crude ash | 7% (3%-8%) |
| vitamin B6 | |

Units are grams per 100 grams of diet
this meal is followed by a carbohydrate snack A diet that mimics the regimen of low protein diet, followed by the second meal of carbohydrate, comprises:

| STANDARD DIET | |
|---|---|
| crude protein | 26% (20%-32%) |
| crude oil | 18% (16%-20%) |
| carbohydrate | 43% (20%-60%) |
| moisture | 8% (2%-10%) |
| crude ash | 7% (2%-8%) |
| vitamin B6 supplement | |
| time-release high glycemic index carbohydrate | 3% (1% to 4$) |

Units are grams per 100 grams of diet

Neutral Branched-Chain Amino Acid Supplements:

The catecholamine/serotonin balance can be tipped toward serotonin by adding at least one of the group consisting of leucine, isoleucine or valine, at a ratio of about 0.5% to 2% dry weight to protein dry weight. The following Table I gives preferred levels for diets of varying protein content

TABLE I

| Approximate protein, grams dry weight in 100 grams diet | Supplemental amino acid, milligrams |
|---|---|
| 15 | 100-250 |
| 20 | 200-300 |
| 25 | 250-375 |
| 30 | 250-500 |

The ratio of branched-chain amino acids to protein is 0.5% to 2%

DETAILED DESCRIPTION OF THE INVENTION

The methods and compositions of this invention were designed to assist mammals which, when domesticated, are forced to alter their natural behavioral repertoires, to resolve the resulting conflicts between normal behavior and that which is expected of a domestic animal. The domesticated mammal must be neither somnolent nor over active. It must be prepared to expend energy in response to its owner's demands, but should not be excitable or aggressive. It is not surprising that many domesticated mammals are stressed, neurotic and may be put down. For instructions on practicing the present invention, the dog has been chosen as the exemplar mammal. A leading cause of dog mortality is euthanasia because of behavioral problems. Well-meaning dog owners may adopt a pet with every intention of keeping the animal for its life span, but due to intolerable behavior, are forced to terminate the relationship. Problem behavior may include excessive barking, failure to house train, anxiety, or aggression. Others may be due to the dog's reaction to being left alone during the day. Many owners simply do not have the time or resources to treat these behaviors with training or to seek professional help. A simple regimen that fits in well with the daily schedule and results in improved learning capacity, mood and behavior can improve the dog's behavior and maintain the pet/owner relationship. A supplemented diet is also provided by this invention.

The brain is very sensitive to any change in the level of glucose in the blood and this is usually under careful control by mobilizing glycogen in the liver when the blood level drops. Low blood glucose is characterized by agitation and aggression.

Likewise, amino acids in the diet directly influence brain activity and behavior by enhancing or reducing the rate of synthesis of serotonin, noradrenaline and dopamine, which are collectively known as monoamine neurotransmitters. This group of monoamines are implicated in mood states, learning mechanisms, arousal levels and behavior. Therefore, the content of their precursor amino acids, tyrosine and tryptophan, in the diet has some effect on the functional activity of the mammalian brain. Tyrosine is the precursor of adrenaline and noradrenaline, which lead to increased activity, excitability and possibly aggression, while tryptophan is the precursor of serotonin, a mood stabilizing neurotransmitter. Surprisingly, it is here shown that supplementing the diet with neutral branched chain amino acids such as leucine is as effective in enhancing serotonin levels in the brain as adding tryptophan to the diet, as measured by improved behavior and learning ability, as is explained more fully below.

However, the concentration of an amino acid in the diet or in the blood does not directly reflect its level in the brain. A complex group of blood-brain barrier mechanisms closely controls both the kinds of substances that enter the extracellular fluid of the brain and the rate at which they enter. Glucose and amino acids, amongst other important substrates, use an active transport mechanism, that is, combining with transport proteins to cross the blood-brain barrier.

For amino acids, these carrier mechanism are both size and charge specific. Within each carrier group, individual amino acids compete with each other for uptake. Hence, an event such as meal ingestion can influence the level in the brain of a given amino acid by modifying its concentration in the blood and/or the blood concentration of other amino acids that compete with it for uptake. Therefore, the ratio of tyrosine of tryptophan to the sum of the other large neutral amino acids in the circulation will effectively control the amount of the amino acid taken across the blood-brain barrier. Competition between tryptophan and other neutral branched-chain amino acids is very important and is a dominant determinant of tryptophan uptake into the brain.

Tryptophan is present in relatively lower amounts in high protein foods compared to other large neutral amino acids such as tyrosine, and therefore, when a meal containing a high concentration of protein is ingested, tyrosine gains a competitive edge for entry into the brain, leading to the production of noradrenaline and the potential for more aggressive behavior. A diet supplemented with the branched-chain amino acids leucine, isoleucine and valine, most preferably leucine, are especially useful in competition with tyrosine and enhancing the uptake of tryptophan.

Conversely, following a high carbohydrate load, tryptophan enters the brain. However, brain tryptophan can only be significantly raised by carbohydrate intake if the carbohydrate second meal is given with two or three hours of protein ingestion. Insulin, secreted in response to carbohydrate ingestion, regulates plasma glucose levels and also diverts other large neutral amino acids to peripheral skeletal tissues where they are involved in energetic and immune system pathways. Adding a time-release high glycemic index carbohydrate to the diet can simulate the second mean. Such carbohydrates are rapidly absorbed and enter glycolysis readily and include but are not limited to monosaccaccharides such as glucose and disaccharides such as sucrose and fructose. It is well known in the art to make a time-released composition by coating particles of the carbohydrate with a substance which is slowly dissolved over the desired time, releasing the carbohydrate. Such substances include but are not limited to hydroxymethylcellulose or gelatine.

Serotonin in the brain is synthesized from tryptophan; however its synthesis depends on certain co-factors being present. Amongst other functions, the B group vitamins maintain the functional integrity of the mammalian nervous system. The enzymes involved in serotonin synthesis are B6 and riboflavin dependent. As the B group vitamins are water soluble and not stored in the body, adequate concentration needs to be provided in the daily diet.

Based on knowledge of the relationship to neurotransmitters to mood, these inventors have developed diets and feeding regimens that have been shown to improve the mood and thus the behavior of dogs. In addition, the invention has surprisingly been shown to increase the animal's learning capacity, which also improves behavior. In summary, the regimen, reduced to its simplest terms, is a program dividing the day's feeding into two parts; a morning feeding of a complete meal having controlled protein content and a supplementation of either leucine or tryptophan, followed several hours later by a carbohydrate second meal. The meal and second meal are repeated later in the day. A supplemented diet, which may be fed as preferred by the owner, is provided, the supplement being at least one of the group consisting of leucine, isoleucine and valine.

The following examples illustrate the regimen and behavioral results of the diets and methods of this invention and are provided for illustrative purposes only, not to define the scope of the appended claims. For purposes of this invention, the term "diet" is meant to refer to the food to be given to the mammal.

Example 1

Supplement to Tip the Catecholamine/Serotonin Balance Toward Serotonin

A low protein diet followed by a carbohydrate supplement may not be suitable for all mammals. For example, a feline requires more protein than the exemplar dog in these examples. Growing, breeding and lactating mammals and those recuperating from illness or trauma, should have a good, adequate diet with adequate protein to satisfy the extra protein demands. An alternative route to achieving the benefits of the low protein/carbohydrate diet is the supplementation of the diet with branched-chain amino acids which compete with tyrosine uptake at the blood/brain barrier to effectively decrease the level of the catecholamine neurotransmitters and increase the level of serotonin, thus achieving mood stabilization and stimulation of cognition. Any or a mixture of leucine, isoleucine or valine is added to a diet in the ratio shown in Table I.

TABLE I

| Approximate protein, grams dry weight in 100 grams diet | Supplemental amino acid, milligrams |
|---|---|
| 15 | 100-250 |
| 20 | 200-300 |
| 25 | 250-375 |
| 30 | 250-500 |

By calculation, the ratio of tyrosine update-competitive amino acid to protein is from 0.5% to 2%.

Example 2

Discrimination Learning

To determine the effect of diet on learning capability, 81 dogs of various ages, types and sex were recruited from dog training clubs and colleagues of the experimenter; however, one dog had to be withdrawn from the study. Inclusion into the study required that the dogs were not receiving any veterinary treatment or medication for behavioral problems. All dogs were in good health, having been fully vaccinated and wormed. Dogs were tested in simple tests that required no lengthy training time. The owner was allowed to be present, although not allowed to direct the dog at any time, to endure that the dog remained as relaxed as possible and that there was as little disruption as possible to each dog's behavioral repertoire. Each dog's baseline learning capability was established on its performance in Test A. It was determined that 15 of the dogs were fast learners, while 65 were slow learners.

Slow learners, those 65 dogs which did not achieve success within five minutes (300 seconds) were randomly assigned to one of three test diets (A, B, and C) or remained on their existing diet, the last group serving as control. Each owner was supplied an information sheet advising how to introduce the new diet over a period of days, to ensure that no digestion problems occurred from a sudden change of food. The dogs remained on the assigned diet for a period of three weeks and their learning capability was re-evaluated according to their performance in Test B. Latency to learn the task was used as a measure of learning capability and specific displacement activities were monitored to evaluate the effect on various behavior patterns. Both test were carried out at similar times of day to avoid any diurnal variations in amino acids affecting the performance of the dog and post prandial fluctuations on the availability of tryptophan in the brain.

Food pellets of their assigned diets were used as rewards, and their palatability for each dog was established prior to testing. The identical type, size and amount of food pellets was used throughout the study to avoid any contrast effects on response rate. Each test was carried out in the same environment to ensure that any distractions were constant for both tests.

The dogs' latency to learn was measured in the time it took them, to achieve success, measured as 100% of correct responses in five consecutive trials. Test A, the detour test, was considered to be successfully performed when the dog inserted a minimum of head and shoulders into the compartment. Test B, the T-maze test, was considered to be successfully performed when the dog inserted a minimum of head and shoulders into the arm of the "T". Behavior patterns were measured by the presence or absence of a specific behavior rather than frequency, due to the variations in time for each test. The experimenter was present in the room at all times for recording purposes; observer reliability was maintained as the same experimenter was present throughout both tests. The experimenter did not interact with the dog at any time and was not associated with any piece of equipment to avoid any subtle influence on the performance of the dog.

The diets tested were: Diet A, standard diet supplemented with 300 mg leucine/100 grams w/w product; Diet B, standard diet supplemented with 300 mg tryptophan/100 grams w/w; Diet C, standard diet with no supplements. The performance of dogs maintained on their regular diet would indicate whether the dietary changes tested were not significant in canine learning and behavior.

A. Detour Test

The dog was placed in front of a three-compartment box two feet wide, four feet long and three feet high, in a position to view all three compartments simultaneously, giving them the choice to enter any compartment. Each compartment was equipped with a light and a hatch for delivery of a food pellet. A correct choice, dependent on the presence of a flashing light, was rewarded by a food pellet. Spontaneous walking into the compartments was infrequent and therefore, learned response was easily identified. A correct response was recorded when the dog had at least its head and shoulders into the correct compartment. An incorrect response was recorded when the dog made the wrong choice or did not make sufficient movement into the compartment.

B. T-Maze Test this test was designed as an "object permanence" test to ascertain the ability of the dog to learn and remember the process of locating a hidden object. The dog was placed in front of a two-compartment, T-shaped box comprising a decision channel and two arms at right angles to the decision channel. The decision channel was equipped with a light on each side and was separated into two channels beyond the level of the lights. The dog was in a position to view both sides of the entrance channel, but could not see into the two arms. When the dog approached the decision channel, it was free to proceed to either arm, but could observe the object being hidden. When one or the other light would flash, if the dog chose to enter the arm on that side, it would be rewarded with a food pellet via the hatch in each arm. The dog would be evaluated on the correct choice of arms. The test was more difficult than Test A as food was more remotely delivered through a hatch in an arm which could not be viewed by the dog until after a choice was made. The dog was considered to have made a correct response when its head and shoulders were in the correct arm of the T-maze. An incorrect response was recorded if the dog made a wrong choice or did not make sufficient movement into the correct arm.

The four groups of slow learners were compared at the beginning of the trials and again after three weeks on the assigned diets and the results also compared to the fast learner groups. The performance in Test B of the slow learners assigned to Diet A became as good as that of the fast learners, indicating significant improvement in learning.

Example 3

Representative Case Studies

A. Aggression/over-reactivity. A Cocker Spaniel bitch, 12 months old, first showed signs of aggression at 8 weeks of age. She now guards anything, including her lead. Whenever the owners pass near her, if there is an object she is guarding nearby, she will fly at them. She enjoys playing fetch but will not let go of the article. She has had some training and will sit and come when called. She was put on the low protein diet with the second meal of carbohydrate. Specific retrieve games to gain more cooperation and intervention when an outburst was imminent were taught. The intervention comprised being taught to run into the kitchen and sit for a reward. Within seven days, the "tantrums" stopped and only one incidence of growling had occurred. It was estimated that the improvement in the first week was about 80%.

B. Attention deficit hyperactivity. A cross-bred castrated male, obtained from a rescue center three years ago and now four years old, is continually active. He paces, barks, jumps up and paws in an effort to gain attention and attempts to escape from any open door or window. The dog can keep up this behavior 18 hours a day. Basic training, time-out periods and simple obedience exercises, has proved difficult as the dog does not appear to have the capacity to retain information. The dog was put on the low protein diet with the second meal of carbohydrate. Within 4 days, he lies calmly when a "time-out" signal is given and has begun to respond well to basic obedience training. His general activity has been reduced and he is responding well to basic training and is learning new commands.

C. Separation anxiety. A German Short-hair Pointer bitch, seven months old, is very stressed when left alone. She howls, barks and becomes agitated and destructive. Training in time out periods to habituate her to isolation are only slightly effective; after three weeks, she is slightly improved but can be left for a maximum of 15 minutes before howling and being destructive. After being put on the low protein diet followed by the second carbohydrate meal, within 21 days, she is so confident when left alone for anything up to three hours, that she is often lying quietly and is sometimes asleep when her owners get home.

Example 4

Supplementation with Amino Acids and/or Time-Release Carbohydrate

The benefits of the meal/second meal regimen and the low protein diets may be duplicated. Since the ratio of tyrosine to branched chain amino acids is the key to decreasing tyrosine uptake in the brain, rather than the absolute level of tyrosine ingestion, it is possible to replicate the results found with the low protein diet with supplementation of any diet with the branched chain amino acids leucine, isoleucine and/or valine. Additionally, the incorporation of a carbohydrate that is time released two to three hours after ingestion will result in the benefits of the meal/second meal regimen.

Example 4

Application to Horses

The horse, in its natural state, co-exists in a herd, wandering in search of food, grazing constantly, expending high levels of energy only sporadically, as in fleeing danger or migrating rapidly to find new food sources. The modern horse is in a very different environment. The normal behavioral repertoire and opportunity for social interaction with the herd is now restricted and the type and amount of food is now controlled by the owner. The horse must respond promptly with high levels of energy to the owner's command, be it work, racing or training and therefore must be neither sluggish nor hyperexcited.

The stabled horse is fed a high concentrate diet containing a large proportion of carbohydrate as starch, making the efficiency of the small intestine digestion more significant than that of the horse on its natural diet of grass, which has only a low starch content. Starch is a glucose polymer, which must be converted to glucose before being absorbed into the blood stream. It can be a problem for the horse to break down the glucose-glucose bonds in the short time that the material is in the small intestine. If the starch is not all digested and passes to the large intestine, problems such as laminitis or colic may occur. Therefore, the standard horse diet includes cooked starch in extruded or micronized feeds, which are easier for the horse to digest.

Owners of competition horses must constantly balance energy availability and over-excitability when competing. The ideal competitive horse responds well to direction, is energetic but not easily excited or distracted. The horse diet is, compared to that recommended above for the dog, already low in protein. When the horse is to be called upon for energy, it is fed extra proteins, in the form of oats. As discussed above, protein generally contains higher tyrosine (the catecholamine precursor and aggression promoter) than tryptophan (the serotonin precursor and calming promoter). Any increase in protein tends to excite the horse. Tryptophan enhanced diets are readily available to correct this imbalance, but some studies have shown curiously anomalous results: low doses cause mild excitement, whereas high doses reduce endurance capacity and may cause hemolytic anemia if given orally, presumably due to a toxic hindgut metabolite. Magnesium calmers are also readily available in a variety of forms to be administered orally, but as yet no complete feed has been produced which addresses the problem of suitable balance between tyrosine and tryptophan.

As is seen in the dog, branched-chain amino acids, exemplified by leucine, added to the feed in the proportions of Example 1, Table I, will stabilize the horses' moods and such supplementation is expected to increase cognitive ability. The supplemented feed can be fed routinely, without the need for administration by buccal syringe before competition.

For purposes of illustration, the dog has been selected as the test animal, but it is understood that the principles of this invention may also be applied to other mammals, including domestic felines and humans. Those skilled in the art may make modifications to the diets and regimen described herein, but such modifications are considered to be within the scope of the appended claims. The teachings of all references cited herein are incorporated by reference in their entirety.

We claim:

1. A method of controlling the mood and behavior of a mammal comprising orally administering a first low protein food meal, followed by a second carbohydrate meal orally administered three hours after the first meal to the mammal, experiencing attention deficit or anxiety, in need of such control, wherein the second meal consists of pasta or potatoes and is about 0.2% of the body weight of the mammal, wherein an improvement in mood and behavior persists for as long as the meals are orally administered to the mammal.

2. The method of claim 1 where the low protein food meal comprises 20 to 26% dry weight of the food and the carbohydrate second meal consists of one-half to four ounces of pasta or potatoes depending on the size of the mammal to be about 0.2% of the body weight of the mammal.

3. The method of claim 2 wherein the mammal is a dog.

4. The method of claim 1 where the first meal is further supplemented with vitamin B6.

5. The method of claim 4 where the vitamin B6 supplement is from 0.05 to 10 mg/body weight of the mammal.

6. The method of claim 1 wherein the method is continued for at least four days.

7. The method of claim 6 where the low protein food meal comprises 20 to 26% dry weight of the food and the carbohydrate second meal comprises one-half to four ounces of pasta or potatoes depending on the size of the mammal to be about 0.2% of the body weight of the mammal.

8. The method of claim 6 where the mammal is a dog.

* * * * *